United States Patent [19]
Coletti

[11] Patent Number: 5,328,469
[45] Date of Patent: Jul. 12, 1994

[54] HYBRID BALLOON ANGIOPLASTY CATHETER AND METHODS OF USE

[76] Inventor: Roger Coletti, 506 Long Dr., Wyckoff, N.J. 07481

[21] Appl. No.: 33,916

[22] Filed: Mar. 19, 1993

[51] Int. Cl.⁵ .................... A61M 29/00; A61M 5/178
[52] U.S. Cl. ...................................... 604/96; 604/165; 606/194
[58] Field of Search .......................... 604/96–103, 604/165; 606/192, 194, 195; 128/656–658

[56] References Cited

U.S. PATENT DOCUMENTS

| | | | |
|---|---|---|---|
| 4,483,340 | 11/1984 | Fogarty et al. | 606/194 X |
| 4,526,175 | 7/1985 | Chin et al. | 606/192 X |
| 4,606,347 | 8/1986 | Fogarty et al. | 606/194 X |
| 4,796,629 | 1/1989 | Grayzel | 604/96 X |
| 4,820,270 | 4/1989 | Hardcastle et al. | 604/96 |
| 4,932,959 | 6/1990 | Horzewski et al. | 604/165 X |
| 5,035,705 | 7/1991 | Burns | 606/194 |
| 5,042,976 | 8/1991 | Ishitsu et al. | 604/96 |
| 5,059,176 | 10/1991 | Winters | 606/194 X |
| 5,085,636 | 2/1992 | Burns | 606/194 X |
| 5,171,297 | 12/1992 | Barlow et al. | 604/96 |
| 5,176,637 | 1/1993 | Sagae | 604/96 |
| 5,176,698 | 1/1993 | Burns et al. | 606/194 |

Primary Examiner—C. Fred Rosenbaum
Assistant Examiner—Frank Wilkens
Attorney, Agent, or Firm—Caesar, Rivise, Bernstein, Cohen & Pokotilow Ltd.

[57] ABSTRACT

A instrument and method for effecting the dilatation of an artery. The instrument comprises a catheter and an expandable balloon. The catheter includes first and second lumens extending longitudinally therethrough and in communication with respective portions of the balloon. The balloon is an everted member having a cylindrical outer wall and a cylindrical inner wall disposed within the outer wall. The inner wall has a central passageway extending therethrough communicating with the first lumen through which a conventional guide wire may be extended. The inner wall of the balloon is collapsible radially inward, e.g., upon the application of a vacuum to the first lumen, whereupon it frictionally engages the guide wire to prevent relative movement therebetween and to enable the instrument and guide wire to be moved as a unit. The outer wall of the balloon is collapsible radially inward, e.g., upon the application of a vacuum to the second lumen, so that its cross-sectional area is less than that of the catheter to facilitate the introduction of the balloon into a restriction, a stenosed area, in the artery. The outer wall of the balloon is also movable radially outward by introducing a pressurized fluid into the annular space in the balloon member via the second lumen to effect the dilatation of the stenosed artery. A cylindrical, radio-opaque stent may be located within the balloon between the inner and outer walls thereof.

32 Claims, 3 Drawing Sheets

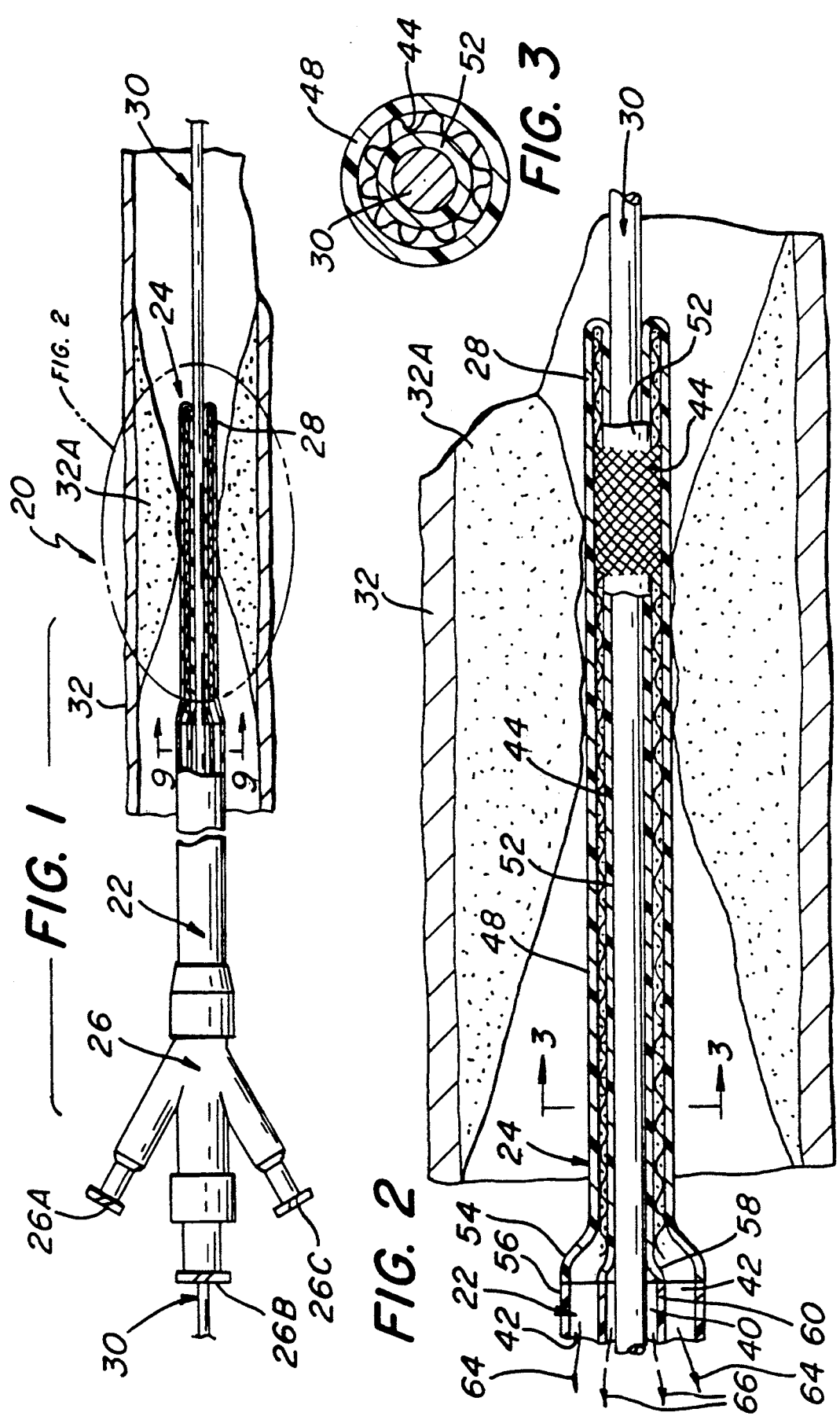

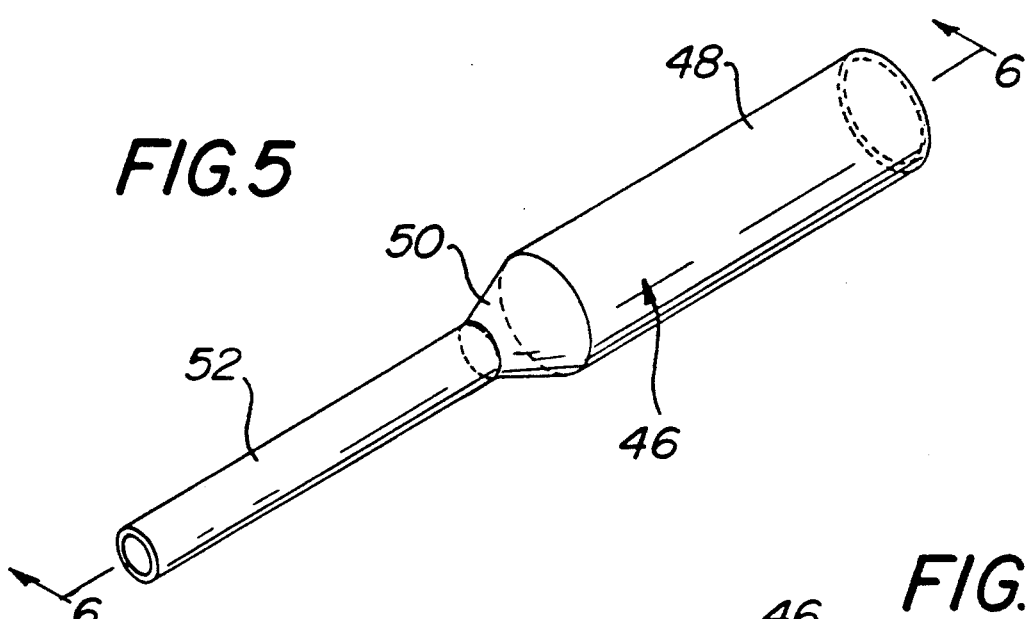
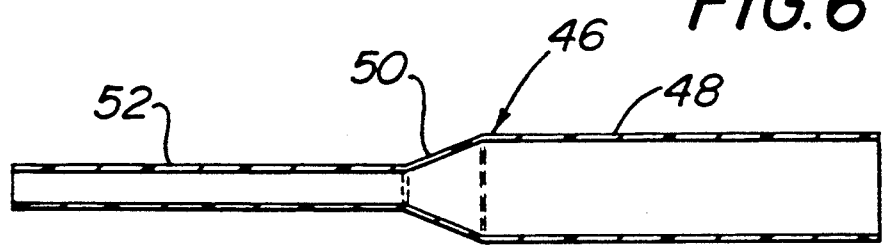
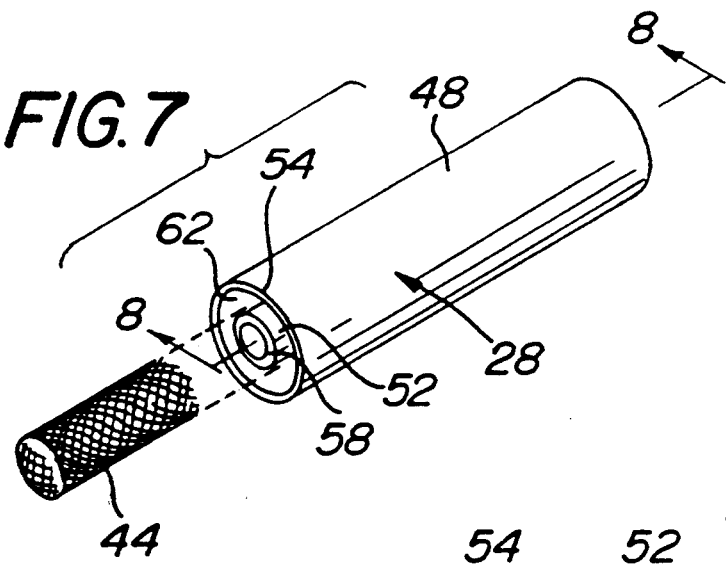
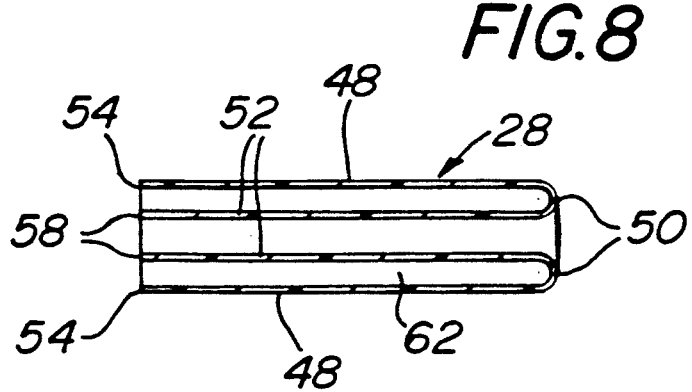

HYBRID BALLOON ANGIOPLASTY CATHETER AND METHODS OF USE

BACKGROUND OF THE INVENTION

This invention relates generally to dilatation catheters, and more specifically to over-the-wire dilatation catheters for angioplast.

Angioplasty is commonly carried out by use of a dilatation catheter which has an inflatable balloon at its distal end. The balloon catheter is typically guided through the patient's vascular system to a location adjacent the stenosis via use of a guide catheter. Then, using some imaging technique, e.g., fluoroscopy, the catheter is moved the remaining distance through the opening in the stenosis, i.e., "across" the stenosis. With the balloon within the stenosis, it is inflated by supplying a fluid, e.g., saline and a radio-opaque dye, whereupon the balloon's inflation stretches the artery and presses the lesion into the artery wall, thereby enabling increased blood flow through the artery.

Balloon angioplasty catheters are of two basic types, namely, the so-called "fixed-wire" type and so-called "over-the-wire" type. The fixed wire balloon catheter essentially comprises an expandable balloon fixedly secured onto a distal end portion of a guide wire. Such an instrument has a very narrow profile or "crossing size", i.e., a small cross-sectional area. Thus, the fixed-wire balloon catheter can easily cross its way through narrowed arteries so long as the tip or distal end can be negotiated through the artery. The major limitation with fixed-wire balloon catheters is the difficulty in steering the balloon wire tip into and through the narrowings or vascular restrictions. Another major limitation is that one balloon cannot be exchanged for another, e.g., a larger balloon, without first removing the first balloon. Such removal is undesirable since rethreading another fixed wire instrument to the vascular position of the first instrument vacated my not be possible or at the very least be difficult and potentially dangerous.

The over-the-wire balloon catheter essentially comprises an elongated catheter having a distal end portion at which an expandable balloon is fixedly secured and a central passageway through which a guide wire can be extended. With such an instrument a guide wire is first passed through the narrowed artery and then the balloon catheter is passed over the guide wire so that the guide wire is within the catheter's central passageway. While over-the-wire balloon catheters allow more flexibility in catheter placement and exchange, i.e., removal of one balloon catheter leaving the guide-wire in place so that a larger balloon catheter and be slid thereon to the vacated position, such catheters are not without their own limitations. In particular, a major limitation of over-the-wire balloon catheter instruments is that the tip crossing size is significantly larger than that of a fixed-wire instrument. Accordingly, the crossing of severely narrowed arteries with over-the-wire balloon catheters is made more difficult if not impossible.

Heretofore considerable efforts have been made to provide an over-the-wire dilatation catheter which is sufficiently flexible to pass through very tight tortuous paths, which exhibits good "pushability" (i.e., the transmission of longitudinal force along the catheter so that it can be readily pushed through the vascular system), and which has a reduced profile so that its balloon not only can reach but also can cross a very tight stenosis. Examples some prior art over-the-wire balloon catheters are found in U.S. Pat. No. 4,606,347 (Fogerty et al.), U.S. Pat. No. 4,863,440 (Chin), U.S. Pat. No. 4,932,959 (Horzewski et al.), U.S. Pat. No. 5,032,113 (Burns), U.S. Pat. No. 5,035,705 (Burns), U.S. Pat. No. 5,045,061 (Seifert et al.), U.S. Pat. No. 5,047,045 (Arney et al.) and U.S. Pat. No. 5,085,636 (Burns).

However, a need still presently exists for a balloon catheter which exhibits the small crossing size advantages of a fixed-wire instrument, with the positioning and exchange advantages of an over-the-wire instrument, all the while exhibiting good flexiblility and pushability.

OBJECTS OF THE INVENTION

Accordingly, it is a general object of this invention to provide a dilatation catheter and methods of use which overcomes the disadvantages of the prior art and meets the above needs.

It is another object of this invention to provide a dilatation catheter which provides the positioning advantages of an over-the-guide wire balloon catheter with the small crossing size advantages of a fixed wire balloon catheter.

It is another object of this invention to provide a dilatation, e.g., balloon angioplasty, catheter whose crossing profile is very small.

It is another object of this invention to provide dilatation, e.g., balloon angioplasty, catheter which is easy to position and use within a lumen, e.g., an artery, of a living being.

It is a further object of this invention to provide a balloon angioplasty catheter which is simple in construction.

It is still a further object of this invention to provide a method for effecting the dilatation of a lumen within the body of a living being by use of an instrument which provides the positioning advantages of an over-the-guide wire balloon catheter with the small crossing size advantages of a fixed wire balloon catheter.

SUMMARY OF THE INVENTION

These and other objects of this invention are achieved by providing a dilatation instrument an method of use, e.g., positioning of the instrument within a stenosed artery in a living being to open it for increased blood flow therethrough.

The instrument comprises a catheter and expandable balloon means. The catheter is an elongated member having a first lumen extending longitudinally therethrough and a second lumen extending longitudinally therethrough. The balloon means comprises a cylindrical outer wall and a cylindrical inner wall disposed within the outer wall. The walls of the balloon means can be formed of an elastic or inelastic material.

The inner wall of the balloon means has a central passageway extending through it and communicating with the first lumen of the catheter member. A guide wire may be extended through the central passageway for relative movement with respect to the catheter.

The inner wall of the balloon means is controllably movable so that it can be in a radially inwardly collapsed state or a radially outward uncollapsed (neutral) state. The inner wall can be moved to the collapsed state in one embodiment of the invention by the application of a vacuum to the first lumen of the catheter. In another embodiment of the invention the inner wall is normally biased in the radially inward collapsed state. Irrespective of how the inner wall is brought to the collapsed state, when it is in that state it frictionally engages the guide wire to prevent relative movement between the guide wire and the catheter so that the guide wire and the instrument can be moved as a unit.

The outer wall of the balloon means is also controllably movable so that it can be in a radially inwardly collapsed state, a "neutral" or uncollapsed state, and a radially outwardly expanded state.

The movement of outer wall of the balloon means to the radially inwardly collapsed state is accomplished by coupling a vacuum to the second lumen. When the outer wall is in the collapsed state its cross-sectional area is less than that of the catheter itself to enable the balloon to be inserted into very small areas.

The movement of the outer wall to the outwardly radially expanded state is accomplished by applying a fluid, e.g., saline, under pressure into the second lumen. When the outer wall is in the expanded state its cross-sectional area is substantially greater than that of the catheter to effect the dilatation of the blood vessel in which it is located.

When the inner wall of the balloon means is moved radially outward to its uncollapsed or neutral state, e.g., by the release of the vacuum from the first lumen of the catheter in one embodiment or by the introduction of a fluid under pressure into that lumen in another embodiment, it disengages from the guide wire so that the catheter member can be moved, e.g., slid along, relative to the guide wire.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 is a side elevational view, partially in section, showing a balloon angioplasty catheter constructed in accordance with this invention extending through a stenosed area in an artery so that the balloon portion thereof can be inflated to open that area to increased blood flow;

FIG. 2 is an enlarged view, partially in section, of the distal portion of the catheter shown within the area bounded by the broken lines in FIG. 1;

FIG. 3 is a sectional view taken along lines 3—3 of FIG. 2;

FIG. 5 is an isometric view of the component making up the balloon of the catheter shown in FIG. 1;

FIG. 6 is a longitudinal sectional view taken along line 6—6 of FIG. 5;

FIG. 7 is an isometric view of the balloon component shown in FIG. 5 after it has been everted to form an annular member for receipt of a cylindrical stent therein;

FIG. 8 is a longitudinal sectional view taken along line 8—8 of FIG. 7;

DETAILED DESCRIPTION OF THE PREFERRED EMBODIMENTS

Figure 4:
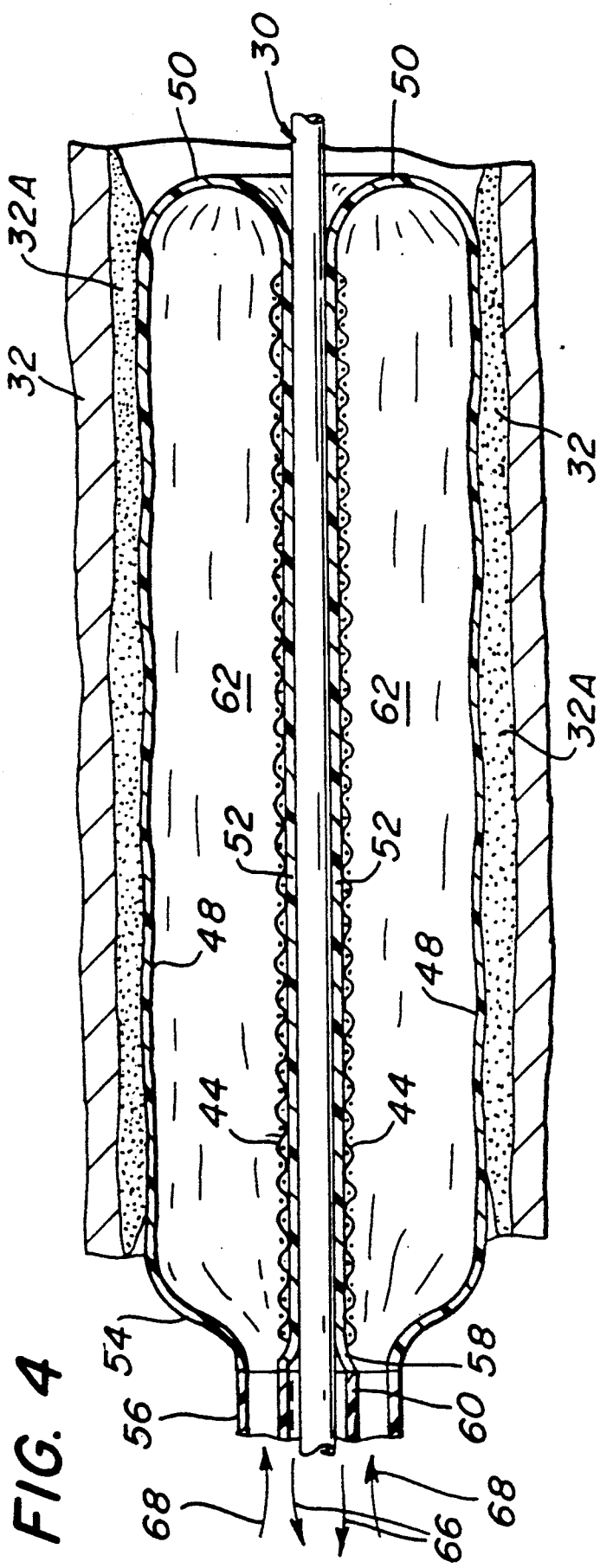
FIG. 4 is a partial sectional view similar to FIG. 2 but showing the distal portion of the catheter after inflation of its balloon.

Referring now to various Figures of the drawing where like reference numerals refer to like parts there is shown at 20 in FIG. 1, one embodiment of a dilatation balloon catheter constructed in accordance with this invention. The catheter 20 basically comprises an elongated dual lumen body 22 having a distal end portion at which a balloon assembly 24 is located, and a proximal portion at which a manifold 26 is mounted. The balloon assembly 24 will be described later. Suffice it to say that the balloon assembly includes a collapsible/expandible (inflatable) balloon 28.

The catheter 20 is arranged to be slid onto and down a conventional guide wire 30 which has been extended through a narrowing or stenosed area 32A in an artery 32 in a similar manner to that of prior art over-the wire catheters so that the catheter's balloon is located adjacent, e.g., just proximally, of the narrowing 32A. However, unlike conventional over-the-wire balloon catheters, the balloon 28 of this invention is arranged to be contracted or collapsed radially to reduce its outside diameter (i.e., crossing profile) so that it may enter through arterial narrowings of a size too small for crossing by conventional over-the-wire balloon catheters. In fact, a catheter constructed in accordance with this invention may utilize a balloon 28 which may be radially collapsed to a size approaching that of a fixed-wire device. For example, the catheter 20 may comprise a balloon whose crossing diameter is only 0.02 inch (0.51 mm), but which can be expanded or inflated to 2 mm for revascularizing an artery.

The catheter 20 of this invention is also constructed so that it may be releasably secured, via friction, to the guide wire 30. In this regard, as will be described in detail later, once the catheter 20 has been slid to the interarterial position so that its balloon 28 is located just proximally of the stenosis 32A, a portion of the balloon can be actuated to frictionally lock it (and, hence, the catheter 20) onto the guide wire 30. Thus, the catheter 20 and the guide wire 30 can be moved as a unit through the narrowing 32A in a similar manner to that of a fixed-wire device, whereupon the collapsed balloon is located within the arterial narrowing 32A, such as shown in FIG. 1. At this point the catheter 20 can be operated to inflate its balloon 28 (like shown in FIG. 4—and which will be described in detail later), to open the stenosed area 32A for increased blood flow therethrough.

The catheter 20 is constructed so that it may be operated at any desired time to release its balloon's frictional engagement with the guide wire so that the catheter can be readily slid along the guide wire. For example, once a stenosed area 32A has been opened by the expansion of the catheter's balloon 28, the catheter 20 may be operated to release the frictional engagement of the balloon with the guide wire 30. This action permits the movement of the catheter to another stenosed area while leaving the guide wire in place, or permits the exchange of that catheter for another while leaving the guide wire in place. For example, once the catheter has been used to open one stenosed area it may be released from the guide wire and slid distally therealong to enter into another stenotic area to effect the opening thereof. If the stenotic area opened by the catheter 20 requires further opening the catheter may be slid proximally on the guide wire to withdraw it from the patient, while leaving the guide wire in place. A larger diameter catheter constructed in accordance with this invention (or even a conventional over-the-wire catheter) can then be slid onto and down the guide wire so that its balloon is located in the now partially open stenosis, i.e., the area vacated by the balloon of the removed catheter. The larger diameter balloon can then be inflated to open that stenosis further.

Figure 9:
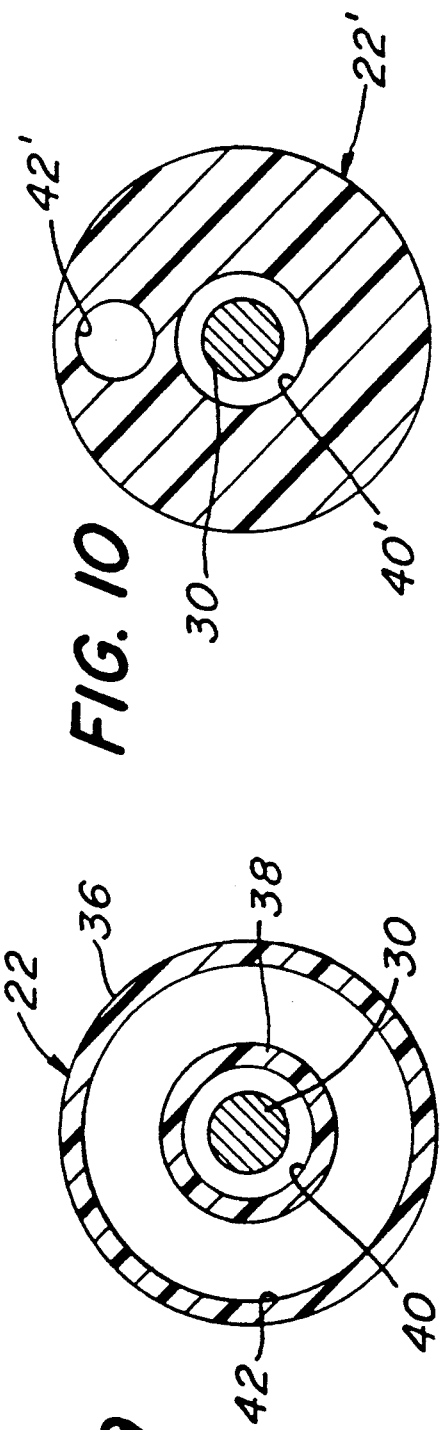
FIG. 9 is an enlarged sectional view taken along line 9—9 of FIG. 1.

Before describing the details of the balloon assembly 24 a brief description of the dual lumen catheter body 22 and the manifold 26 is in order. Thus, as can be seen in FIGS. 1 and 9 the dual lumen body 22 is of conventional construction and basically comprises an outer tube 36 and a concentrically located inner tube 38. Each of the tubes is preferably formed of a flexible material which is somewhat resistant to torsional and longitudinal forces, yet is sufficently flexible to negotiate tight curvatures. The inner tube 36 includes a central passageway or lumen 40 which extends the length of that tube from the manifold 26 to the balloon assembly 24. It is through this lumen that the guide wire 28 passes.

The annular space between the inner tube 36 and the outer tube 38 forms a lumen 42 for effecting the contraction/expansion (inflation) of the balloon 34 by means coupled to the manifold. The manifold 26 can be of any suitable construction, such as that disclosed in U.S. Pat. No. 5,047,045 (Arney et al.), and basically comprises a first port 26A, a catheter guide-wire access port 26B, a second port 26C, and a hemostatic valve (not shown). The port 26A serves as the contraction/expansion (inflation) port for the balloon 28 and is in fluid communication with the lumen 42. In particular, the port 26A is arranged to be coupled to a vacuum source (not shown) to collapse the balloon 28 radially inward when a vacuum is applied to the port 26A. This action decreases the outside diameter of the balloon 28 from a "neutral" or uncontracted size, which is approximately the same as the outside diameter of the catheter body 22, to a "contracted" size, e.g., 0.02 inch (0.51 mm), to enable the balloon to cross very small narrowings. The port 26A is also arranged to be coupled to means (not shown) for providing a conventional balloon inflation fluid, e.g., a solution of a radiopaque dye and saline under pressure, through the port and the communicating lumen 42 to the balloon 28 to inflate it. This causes the balloon to expand to an "expanded" state, e.g., a 2.0 mm outside diameter from a 0.51 mm outside diameter contracted state.

The guide-wire access port 26B is in fluid communication with the guide wire lumen 40 via the hemostatic valve in the manifold 26. Accordingly, the catheter 20 can be threaded onto the guide wire, with the guide wire extending through the port 26B, through the communicating guide wire lumen, and through a portion of the balloon assembly (to be described later) so that a distal end portion of the guide wire is located beyond (distally) of the distal end of the balloon assembly 24. The hemostatic valve within the manifold 26 provides a hemostatic seal at the interface of the guide wire and the manifold when a guide wire is extended therethrough the catheter so that blood can not flow out of the manifold.

The port 26B serves as a means for applying fluid pressure, e.g., a vacuum or pressurized liquid, depending upon the construction of the balloon assembly (as will be described later), to a portion of the balloon 28 to selectively frictionally secure it to the guide wire 30 so that the catheter and the guide wire can be moved as a unit through the vascular system (as mentioned earlier), while also serving to selectively release the catheter from such securement so that the catheter can be slid relative to the guide wire (as also mentioned earlier).

Referring now to FIGS. 1-3 and 7 the details of the balloon assembly 34 will be described. Thus, as can be seen therein the balloon assembly 24 basically comprises the heretofore identified balloon 28, and a cylindrical stent 44. The balloon 28 is an annular member which is formed from a tubular blank of material 46, like that shown in FIGS. 5 and 6. The blank can be formed of of any suitable material used heretofore in balloon catheters, and thus can be resilient (compliant) or non-resilient (non-compliant), as desired. In the embodiment shown herein the blank 46 is of uniform wall thickness and includes a large diameter cylindrical section 48, a conical intermediate section 50, and a small diameter cylindrical section 52. The blank 46 is everted so that the large diameter section 48 is disposed over the small diameter section 52 to form the annular member shown in FIG. 8. In particular, when everted, the large diameter section 48 forms the outer wall of the annular balloon 28, while the small diameter section 52 forms the inner wall of the balloon. The intermediate section 50 is rounded (See FIG. 8) and forms the distal end of the balloon 28. The balloon can be of any desirable length, e.g., from 20 mm to 40 mm long.

As can be seen in FIGS. 2 and 4 the proximal end 54 of the outer wall 48 is secured via any suitable means, e.g., an adhesive, to the distal end 56 of the outer tube 36 of the catheter body 22, while the proximal 58 end of the inner wall 52 is similarly secured to the distal end 60 of the inner tube 38 of the body. The outside diameter of the outer wall 48 of the balloon 28, when in the neutral condition like shown in FIGS. 7 and 8, is approximately the same as that of the outer tube 36 of the catheter body 22. The central lumen 40 of the inner tube 38 is axially aligned with and is preferably of the same inner diameter as that of the inner wall 52 of the balloon 28 to form a passageway extending completely through the catheter 20 for receipt of the guide wire 28, as shown in FIGS. 1, 2, and 4. Thus, in the neutral state the internal diameter of the inner wall of the balloon 28 is slightly larger than the external diameter of the guide wire 30.

The stent 44 is provided to support and stabilize the balloon 28, e.g., prevent it from "accordioning" or otherwise collapsing longitudinally, when the catheter is slid distally along the guide wire to locate it at the stenosis to be opened. The stent 44 basically comprises a cylindrical member which is disposed within the annular space 62 and extends for approximately the full length thereof. The stent is preferably arranged to collapse radially inward when the balloon is collapsed so that it will not interfere with that action. To that end the stent is formed of any suitable material which provides longitudinal stability, is radially collapsable/expandable, and is somewhat flexible longitudinally. In the preferred embodiment shown herein the stent comprises a woven mesh and at least a portion of it is radiopaque to facilitate use of the catheter. In its uncollapsed state the internal diameter of the stent is just slightly larger than the uncollapsed external diameter of the inner wall 52 of the balloon 34 so that it lies closely adjacent thereto.

It should be pointed out at this juncture that a stent may not be required for all angioplasty applications to support and stabilize the balloon during its movement along the guide wire. In this regard when the balloon 28 is in its collapsed state without a stent therein the inner wall 52 and the outer wall 48 of the balloon 28 will engage each other to provide some resistance to longitudinal collapse. If more resistance to longitudinal collapse is deemed desirable or necessary the stent 44 can be utilized. Alternatively, the balloon itself may be constructed to include means for effecting longitudinal support, stability, and resistance to longitudinal collapse. In this regard the section 52 of the blank 46 may be longitudinally fluted and of the same external diameter as the section 48 or it may may be of cylindrical profile and including a plurality of longitudinally extending ribs integrally formed therewith.

Operation of the catheter 20 is as follows. A conventional guide wire 30 is placed within the patient's vascular system in a conventional manner so that its distal end extends through and distally of the stenotic area 32A to be opened. A conventional vacuum or suction source (not shown) is then coupled to the port 26A to evacuate any fluid from the interior 62 of the balloon 28 via the lumen 42 as shown by the arrows 64 in FIG. 2. This action has the effect of collapsing the balloon 28, i.e., drawing the outer wall 48 radially inward toward the inner wall 52, so that the balloon is of minimum outside diameter, i.e., is of its "crossing" diameter. The balloon can then be slid down the guide wire 30 until it is located proximally, yet closely adjacent the stenotic area 32A.

At this time a vacuum from the vacuum source coupled to the port 26A (or from some other source) is coupled to the port 26B. That vacuum is coupled via the central passageway or lumen 40 to the interior of the inner wall of the balloon 28. In particular, the vacuum applied draws whatever fluid(s) are within the lumen 40 and within the space between the balloon's inner wall 52 and the outer surface of the guide wire 30 out of the catheter in the direction of the arrows 66 shown in FIG. 2, whereupon the inner wall 52 of the balloon collapses radially inward and frictionally engages the outer surface of the guide wire as shown in FIGS. 1 and 2. In order to ensure that the balloon begins to collapse radially inward from its free end so that it will collapse along its entire length, the internal diameter of the balloon wall 52 at the distal end of the balloon 28 may be of slightly smaller than the remainder of that wall to create a vacuum seal thereat. Alternatively, the inner wall 52 of the balloon 28, or the stent 44, or both, may be constructed to cause the balloon to preferentially begin collapsing from its distal end upon the application of suction to the balloon via lumen 40.

In an alternative embodiment of a catheter 20 constructed in accordance with this invention the balloon may be operated in an opposite manner that just described to effect the releasable frictional securement to the guide wire. In such an alternative embodiment the balloon 28 is constructed so that its inner wall 52 normally frictionally engages the guide wire 30 and is released from such engagement by the application of fluid under pressure to the lumen 40 of the catheter. To achieve that end the inner wall 52 of the balloon is formed of an elastic or compliant material whose internal diameter is smaller than the external diameter of the guide wire 30. Thus, the natural bias of the material forming the wall 52 will cause it to attempt to collapse radially inward, thereby frictionally engaging the guide wire 30 extending therethrough. In order to release the frictional engagement a fluid, e.g., saline, under pressure is introduced into the port 26C and down the communicating lumen 40. This action moves the inner wall 52 of the balloon radially outward against its natural bias, thereby releasing the frictional engagement between the balloon and the guide wire to permit the catheter to be slid to the desired position on the guide wire. Once in that position no further fluid is introduced into the port 26C, and whatever fluid had been introduced into the central lumen 40 exits from the open distal end of the balloon, whereupon the inner wall 52 of the balloon collapses inward radially to frictionally engage the guide wire.

In either embodiment of the catheter 20 once the inner wall 52 of the balloon 28 has collapsed so that it frictionally engages the guide wire 30, the catheter and the guide wire are ready to be moved as a unit distally in the same manner as accomplished by a fixed-wire device. Accordingly, the catheter is now slid distally so that the balloon balloon 28, with its outside diameter reduced to the "crossing" diameter, is extended into and through the arterial narrowing 34A as shown in FIGS. 1 and 2. At this time, the balloon can be inflated, and, if desired, the frictional engagement of the catheter 20 and the guide wire 30 released. In any event the inflation of the balloon 28 is effected by releasing the vacuum from port 26A, then applying the inflation fluid, e.g., saline and dye solution, under pressure from means (not shown) into that port and through lumen 42 in the direction of arrows 68 in FIG. 4. This action causes the outer wall 48 of the balloon 28 to move outward radially to the position shown in FIG. 4, thereby compressing the stenotic material to provide a larger opening therethrough.

Once the balloon has completed its task to enlarge the passageway through the stenotic area it may be deflated by withdrawing the inflation fluid from its interior 62 via the port 26A. The catheter 20 can then be withdrawn from the patient by sliding it proximally along the guide wire or may be moved to another stenotic area by sliding it distally along the guide wire until the balloon is just proximally of that area (assuming, of course, in either case that the frictional engagement between the inner wall of the balloon and the guide wire has been released).

Figure 10:
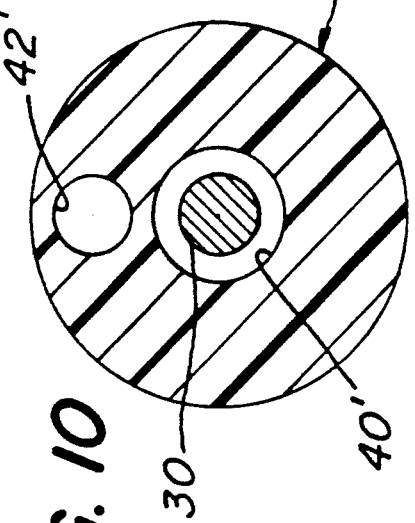
FIG. 10 is a sectional view, similar to FIG. 9, but showing an alternative embodiment of a portion of the catheter of this invention.

In FIG. 10 there is shown an alternative embodiment of a dual lumen catheter body for use in the catheter 20. The body shown in FIG. 10 is designated by the reference numeral 22' and basically comprises an elongated member formed of any suitable material and having a distal end at which the balloon assembly 24 is secured. The body 22' includes a central lumen 40' extending the length of the catheter from the manifold 26 to the balloon 28. The lumen 40' corresponds to the lumen 40 of the catheter body 22 described heretofore, and hence is arranged to receive the guide wire 30 therein and to effect either the frictional securement or the release of the inner wall 52 of the balloon 28 with the guide wire. Thus the lumen 40' communicates with the interior of the inner wall 52 of the balloon 28. The body 22' also comprises a second lumen 42' extending the length thereof. The lumen 42' serves the same function as the lumen 42 described heretofore, but is of slightly different construction. In this regard it is of circular cross section (instead of an annular cross section) and is offset laterally of the central lumen 40' (instead of being concentrically disposed thereabout). The lumen 42' is in fluid communication with the interior 62 of the balloon 28.

Without further elaboration the foregoing will so fully illustrate my invention that others may, by applying current or future knowledge, adapt the same for use under various conditions of service.

I claim:

1. A dilatation instrument comprising a catheter member, fluid pressure means, and expandable balloon means, said catheter being an elongated member having a first and second lumens extending longitudinally therethrough, said balloon means comprising a cylindrical outer wall and a cylindrical inner wall disposed within said outer wall, said inner wall having a central passageway extending therethrough communicating with said first lumen of said catheter member and through which a guide wire may be extended, said fluid pressure means being coupled to at least one of said lumens for controlling the position of said inner wall of said balloon means to move said inner wall to a collapsed and an uncollapsed state, said inner wall when in said collapsed state frictionally engaging said guide wire to prevent relative movement between said guide wire and said catheter member, said inner wall when in said uncollapsed state disengaging from said guide wire to enable relative movement between said guide wire and said catheter member, said coupling of said fluid pressure means to at least one of said lumens also controlling the position of said outer wall by moving said outer wall to a neutral state, a collapsed state, and an expanded state, said outer wall when in said collapsed state having a cross-sectional area smaller than the cross-sectional area of said catheter member, said outer wall when in said expanded state having a cross-sectional area substantially greater than the cross-sectional area of said catheter, said outer wall when in said neutral state having a cross-sectional area greater than when in said collapsed state but less than when in said expanded state.

2. The instrument of claim 1 wherein said inner wall is normally in said neutral state and wherein said fluid pressure means provides a vacuum to said first lumen to cause said inner wall to move to said collapsed state.

3. The instrument of claim 1 wherein said inner wall is normally biased into said collapsed state and wherein said fluid pressure means provides a liquid into said first lumen to cause said inner wall to move to said neutral state.

4. The instrument of claim 2 wherein said inner wall and outer wall are coupled together so that when said inner wall is in said collapsed state said outer wall is in said collapsed state.

5. The instrument of claim 3 wherein said inner wall and outer wall are coupled together so that when said inner wall is in said collapsed state said outer wall is in said collapsed state.

6. The instrument of claim 1 wherein said outer wall is normally biased into said neutral state and wherein said fluid pressure means provides a vacuum to said second lumen to cause said outer wall to move to said collapsed state.

7. The instrument of claim 1 wherein said outer wall is normally biased into said neutral state and wherein said fluid pressure means provides a fluid under pressure into said second lumen to cause said outer wall to move to said expanded state.

8. The instrument of claim 6 wherein said outer wall is normally biased into said neutral state and wherein said fluid pressure means provides a fluid under pressure into said second lumen to cause said outer wall to move to said expanded state.

9. The instrument of claim 2 wherein said outer wall is normally biased into said neutral state and wherein said fluid pressure means provides a vacuum to said second lumen to cause said outer wall to move to said collapsed state.

10. The instrument of claim 2 wherein said outer wall is normally biased into said neutral state and wherein said fluid pressure means provides a fluid under pressure into said second lumen to cause said outer wall to move to said expanded state.

11. The instrument of claim 9 wherein said fluid pressure means provides a fluid under pressure into said second lumen to cause said outer wall to move to said expanded state.

12. The instrument of claim 3 wherein said outer wall is normally biased into said neutral state and wherein said fluid pressure means provides a vacuum to said second lumen to cause said outer wall to move to said collapsed state.

13. The instrument of claim 3 wherein said outer wall is normally biased into said neutral state and wherein said fluid pressure means provides a fluid under pressure into said second lumen to cause said outer wall to move to said expanded state.

14. The instrument of claim 12 wherein said fluid pressure means provides a fluid under pressure into said second lumen to cause said outer wall to move to said expanded state.

15. The instrument of claim 1 wherein said balloon means comprises a distal end, with said central passageway having an open end at said distal end of said balloon means, and wherein said balloon means is constructed so that said inner wall commences collapsing radially inward adjacent said open end of said balloon means to move to said collapsed state.

16. The instrument of claim 1 wherein said balloon means comprises an everted balloon.

17. The instrument of claim 1 additionally comprising means for longitudinally supporting and stabilizing said balloon means from longitudinal collapse upon movement of said catheter along said guide wire in the distal direction.

18. The instrument of claim 17 wherein said last mentioned means comprises a stent located between said inner and outer walls of said balloon means.

19. The instrument of claim 18 wherein said stent comprises a cylindrical member formed of a mesh.

20. The instrument of claim 18 wherein at least a portion of said balloon assembly is radiopaque.

21. A method of positioning a dilatation instrument within a lumen in the body of a living being, said instrument comprising a catheter member and expandable balloon means, said catheter member being an elongated member having first and second lumens extending longitudinally therethrough, said balloon means comprising a cylindrical outer wall and a cylindrical inner wall disposed within said outer wall and defining a space therebetween, said inner wall having a central passageway extending therethrough communicating with said first lumen of said catheter member, said second lumen communicating with said space within said balloon means, said method comprising inserting a guide wire through first lumen and said central passageway, controlling fluid pressure in said second lumen to cause said outer wall of said balloon means to collapse radially inward, whereupon the cross-sectional area of said outer wall is less than the cross-sectional area of said catheter member, controlling fluid pressure in at least one of said lumens to cause said inner wall to frictionally engage said guide wire to preclude relative movement between said catheter member and said guide wire, and moving said catheter member and said guide wire as a unit to a predetermined position within the lumen of said living being.

22. The method of claim 21 additionally comprising controlling fluid pressure in said second lumen to cause said outer wall of said balloon means to move radially outward so that the cross-sectional area of said outer wall is substantially greater than that of said catheter.

23. The method of claim 22 additionally comprising controlling fluid pressure in at least one of said lumens to cause said inner wall to disengage from frictional engagement with said guide wire to enable said catheter member to be moved relative to said guide wire.

24. The method of claim 22 comprising applying a vacuum to said first lumen to cause said inner wall to frictionally engage said guide wire.

25. The method of claim 22 wherein said inner wall normally frictionally engages said guide wire and wherein said method additionally comprises applying a fluid under pressure to said first lumen, whereupon said frictional engagement of said inner wall with said guide wire is released.

26. The method of claim 21 wherein the controlling of fluid pressure in said second lumen to cause the outer wall of said balloon means to collapse radially inward is accomplished by applying a vacuum to said second lumen of said catheter member.

27. The method of claim 22 wherein the controlling of fluid pressure in said second lumen to cause the outer wall of said balloon means to collapse radially inward is accomplished by applying a vacuum to said second lumen of said catheter member.

28. The method of claim 27 wherein the controlling of fluid pressure in said second lumen to cause the outer wall of said balloon means to move radially outward is accomplished by applying a fluid under pressure to said second lumen of said catheter member.

29. The method of claim 24 wherein the controlling of fluid pressure in said second lumen to cause the outer wall of said balloon means to collapse radially inward is accomplished by applying a vacuum to said second lumen of said catheter member.

30. The method of claim 29 wherein the controlling of fluid pressure in said second lumen to cause the outer wall of said balloon means to move radially outward is accomplished by applying a fluid under pressure to said second lumen of said catheter member.

31. The method of claim 25 wherein the controlling of fluid pressure in said second lumen to cause the outer wall of said balloon means to collapse radially inward is accomplished by applying a vacuum to said second lumen of said catheter member.

32. The method of claim 31 wherein the controlling of fluid pressure in said second lumen to cause the outer wall of said balloon means to move radially outward is accomplished by applying a fluid under pressure to said second lumen of said catheter member.

* * * * *